US006421550B1

(12) United States Patent
Bridges et al.

(10) Patent No.: US 6,421,550 B1
(45) Date of Patent: *Jul. 16, 2002

(54) MICROWAVE DISCRIMINATION BETWEEN MALIGNANT AND BENIGN BREAST TUMORS

(75) Inventors: Jack E. Bridges, Park Ridge, IL (US); Susan Hagness, Madison, WI (US); Allen Taflove, Wilmette; Milica Popovic, Evanston, both of IL (US)

(73) Assignee: Interstitial, L.L.C., Prospect, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/120,749

(22) Filed: Jul. 23, 1998

Related U.S. Application Data

(63) Continuation-in-part of application No. 08/641,834, filed on May 2, 1996, now Pat. No. 5,829,437, and a division of application No. 08/492,998, filed on Jun. 21, 1995, now Pat. No. 5,704,355, and a division of application No. 08/269,691, filed on Jul. 1, 1994, now abandoned.

(51) Int. Cl.[7] .................................................. A61B 5/05

(52) U.S. Cl. ....................................... 600/407; 324/638

(58) Field of Search .............................. 600/407, 430, 600/549; 324/637–639

(56) References Cited

U.S. PATENT DOCUMENTS

| | | | |
|---|---|---|---|
| 4,641,659 A | * 2/1987 | Sepponen | 600/430 |
| 4,774,961 A | * 10/1988 | Carr | 600/549 |
| 5,662,110 A | * 9/1997 | Carr | 600/407 |
| 5,829,438 A | * 11/1998 | Bridges | 600/430 |
| 5,841,288 A | * 11/1998 | Meaney et al. | 600/407 |
| 5,983,124 A | * 11/1999 | Carr | 600/407 |

OTHER PUBLICATIONS

S. C. Hagness, A. Taflove, and J. E. Bridges, "Wideband ultra–low reverberation antenna for biological sensing," Electronics Letters, Sep. 11, 1997, pp. 1594–1595, vol. 33.

S. C. Hagness, A. Taflove, and J.E. Bridges, "Two–dimensional FDTD analysis of a pulsed microwave confocal system for breast cancer detection: Fixed–focus and antenna–array sensors," IEEE Transactions on Biomedical Engineering, Dec. 1998, pp. 1470–1479, vol. 45.

S. C. Hagness, J.E. Bridges and A. Taflove, "FDTD analysis of a pulsed microwave confocal system for breast cancer," Proceedings of the International Conference of the IEEE EMBS, Oct.–Nov. 1997, pp. 2506–2508, Chicago, IL.

S. C. Hagness, A. Taflove and J.E. Bridges, "FDTD modeling of a coherent addition antenna array for early–stage detection of breast cancer," IEEE AP–S International Symposium Digest, Jun. 1998, pp. 1220–1223, Atlanta, GA.

(List continued on next page.)

Primary Examiner—Ruth S. Smith
(74) Attorney, Agent, or Firm—McAndrews, Held & Malloy, Ltd.

(57) ABSTRACT

A non-invasive method to detect vascularization associated with one or more malignant tumors in living tissue of a living organism, where dielectric properties of the vascularization are different than dielectric properties of normal living tissue. In one embodiment, a non-ionizing input wave within a wide band frequency range is generated, and the input wave is applied to a field excitation antenna to illuminate a discrete volume within the living tissue of the living organism and to develop scattered power returns from the discrete volume. A receiving antenna then collects at least a portion of the scattered power returns. The scattered power returns are detected and then applied to a signal processor to develop a segregated signal, which is then processed in order to identify the vascularization associated with one or more malignant tumors.

16 Claims, 6 Drawing Sheets

OTHER PUBLICATIONS

M. Popovic, S.C. Hagness, A. Taflove, and J.E. Bridges, "2–D FDTD study of fixed–focus elliptical reflector system for breast cancer detection: Frequency window for optimum operation," IEEE AP–S International Symposium Digest, Jun. 1998, pp. 1992–1995, Atlanta, GA.

TransScan Q&A Frequently Asked Questions TS–2000.
\*\*All of the first five references were previously submitted. It is only the TransScan brochure that we are submitting along with this form.

\* cited by examiner

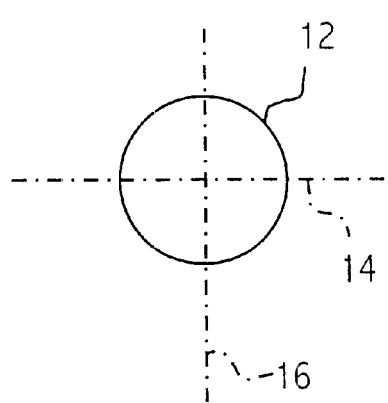
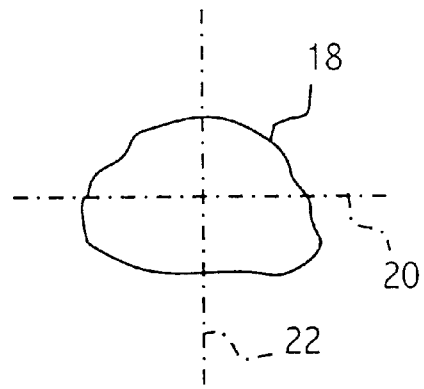
FIG. 1A  FIG. 1B
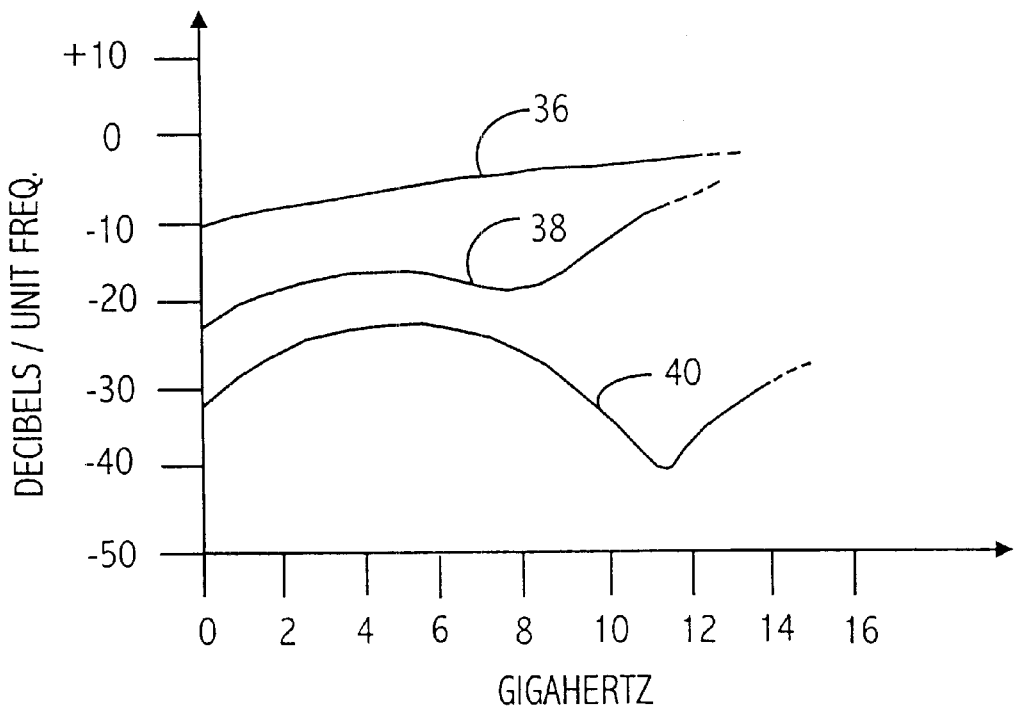
FIG.2

MICROWAVE DISCRIMINATION BETWEEN MALIGNANT AND BENIGN BREAST TUMORS

This application is a continuation-in-part of Ser. No. 08/641,834, May 2, 1996, now U.S. Pat. No. 5,829,437, which is a continuation-in-part of Ser. No. 08/492,998, Jun. 21, 1995, now U.S. Pat. No. 5,704,355, which is a continuation-in-part of Ser. No. 08/269,691, Jul. 1, 1994, abandoned.

BACKGROUND OF THE INVENTION

Early detection and subsequent treatment of breast cancer can have a significant impact on improving the length and quality of life of those afflicted with this disease. Approximately eighty million women should receive annual screening for breast cancer. In actual fact, approximately twenty-five million breast cancer mammograms are performed annually in the U.S. Most of the mammograms are performed with X-ray technology. Of the women screened, the initial mammograms identify some 2,300,000 women as having a suspicious breast mass. Follow-up mammogram diagnosis, again by X-ray mammogram, identifies some 165,000 women as having a tumor; biopsies are then conducted to determine whether the tumor is malignant or benign. The biopsies identify about 41,000 malignant tumors.

Two major problems exist. One is false negatives that are found during the initial X-ray mammogram screening exam. According to the Federal Food and Drug Administration ("FDA"), screening mammography examinations fail to detect some 11,500 malignant tumors [false negatives]. During the mammography diagnostic exams, some 4,400 additional malignant tumors are not detected. The result is that some 16,000 women who have been examined may have a malignant tumor and not know it.

The second major problem is false positives. The X-ray mammography screening process will show some 2,260,000 false positives [indications of suspicious masses]. Those patients with suspicious masses, according to the FDA, may next undergo a diagnostic mammography exam; this procedure may generate 165,000 positive indications. Up to 165,000 biopsies are needed to determine which of the identified tumors are malignant and which are benign. Of this number, the biopsies will show about 125,000 are false positive [benign tumors] and 40,000 are true positive [malignant tumors]. The biopsies are costly; moreover, they introduce anxiety and uncertainty for the patients.

A number of conventional technologies have been proposed to help resolve benign tumors from malignant tumors. Ultrasound and MRI are both used for this purpose. However, ultrasound equipment is expensive and is currently approved to characterize the malignancy of only the larger tumors. MRI equipment is even more expensive and may often require injection of a contrast agent. Other methods sense tumor-induced low-frequency potentials or impedance changes on the surface of the breast. Such methods have been clinically tested but have failed thus far to obtain FDA approval. Sensing tumor-induced infrared emission from the surface of the breast is also being studied. However, past clinical trials with the infrared method have not proved promising.

Methods and apparatus have been considered to characterize tissues, especially to detect or image breast cancers. These are described in U.S. Pat. No. 5,704,355, issued to Jack E. Bridges and entitled "*Non Invasive System for Breast Cancer Detection*" and in two pending patent applications of Jack E. Bridges entitled "*Microwave Method to Detect and System to Detect and Locate Cancer in Heterogeneous Tissues*", U.S. Ser. No. 08/641,834, now U.S. Pat. No. 5,829,437 and "*Breast Cancer Detection, Imaging and Screening by Electromagnetic Millimeter Waves*", U.S. Ser. No. 08/843,858 now U.S. Pat. No. 5,807,257. The technology described in the aforesaid patent, and in the aforesaid pending patent applications, is incorporated by reference in this application.

SUMMARY OF THE INVENTION

One objective of this patent application is to describe improvements in the above noted patent and pending applications that will characterize the differences between malignant and benign tumors. A second objective is to describe techniques that will detect the vascularization that indicates the presence of an incipient malignant tumor, however tiny it may be.

The above-noted microwave technology contrasts tissues based primarily on electrical characteristics determined at least in part by their water content. The differing water content between normal and malignant breast tissues results in an order of magnitude increase in the scattering characteristics of a tumor relative to normal breast tissue. Thus microwave method "sees" the entire tumor, because the tumor has a high water content. In the case of X-ray mammography, the scattering cross-sections are much smaller than for microwave examination. X-ray mammography often can detect a malignant tumor only if micro calcifications are present. Likewise, ultrasound equipment suffers from a lack of contrast between different (malignant of benign) soft tissues.

Similarly, a single antenna may be moved over the breast to create a synthetic aperture array. Such an array can produce signals which, when properly processed, can detect and/or image a tumor.

Other high water content tissues may also be detected or imaged by any of the above-noted systems. For example, some but not all benign tumors can also have a substantial water content. Muscle tissue and arteries, veins and capillaries can also have a high water content. These tissues may also be either detected or imaged by the above-noted microwave system.

As described in the above-noted Bridges patent and pending applications, the functions of detection and imaging can be enhanced by use of differences in the back, forward, and side scatter polarization effects and spectral responses. Not described is how these responses can be used to discriminate malignant from benign tissue. Also not described is how other tumor related phenomena, such as angiogenesis, can be exploited, not only to characterize the nature of a sensed or imaged tumor, but also to help detect the vascularization that indicates the presence of tiny incipient malignant tumors. Further, the need to develop data on the tissues near a tumor, and especially between the tumor and adjacent blood vessels, is not fully discussed.

It therefore is an object of this invention to show how the system and methods of the above-noted patent and pending applications of Bridges can be improved and applied to characterize the nature of tumors and to enhance the detectability of very small tumors. The methods and apparatus described in the Bridges patent and pending applications can be used to characterize geometric features unique to malignant tumors. These are based on (1) geometric differences between benign and malignant tumors, (2) the presence of capillaries in the tissue near a malignant tumor, and (3) the presence of a network of capillaries, tiny veins and perhaps an artery between the malignant tumor and major blood supply vessels. The method, as well as the apparatus, can be further modified to characterize or image the tissues surrounding a possible tumor, especially the tissues between a possible tumor and a small vein or artery.

BRIEF DESCRIPTION OF THE DRAWINGS

FIGS. 1A and 1B are schematic illustrations of a benign tumor and a malignant tumor, respectively;

FIG. 2 is a chart of relative decibels as a function of frequency;

DETAILED DESCRIPTION OF THE INVENTION

Processing Returns from a Tumor

Figure 3:
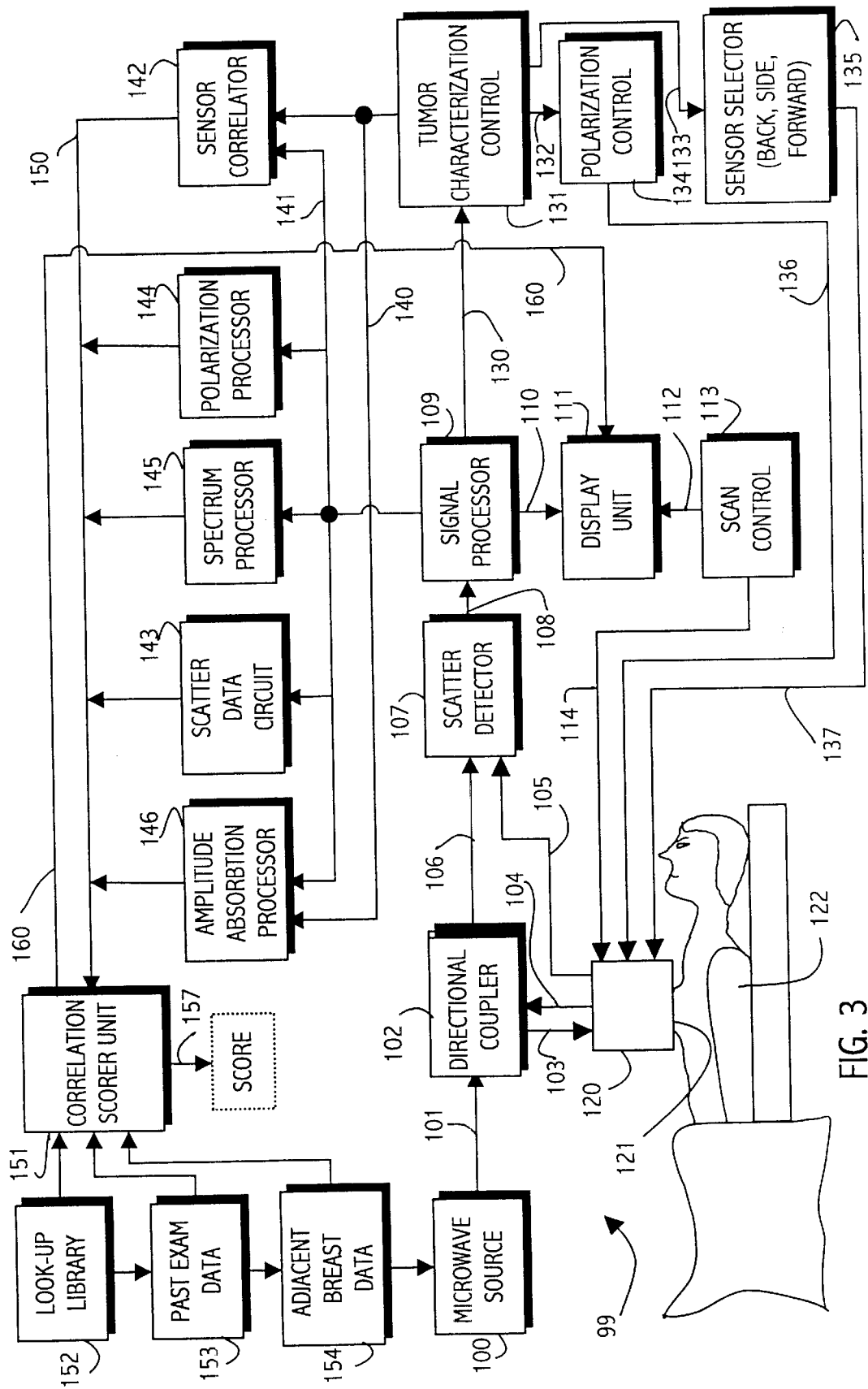
FIG. 3 is a block diagram of a microwave breast examination system illustrating features of the present invention.

Some benign tumors may mimic, in varying degrees, the scatter response signals characteristic of a malignant tumor. Geometrical differences exist between malignant tumors and some benign tumors because benign tumors, too, can have a high water content. In some cases, benign tumors are spherical, whereas malignant tumors are more likely to be asymmetrical and to have rough surfaces. An incipient malignant tumor can grow within the mammary gland ducts, and may have a more rod-like appearance. The asymmetry of the tumor can be developed, for image purposes, by changing the polarization of the impinging electromagnetic wave or by noting the polarization of the scattered (reflected) wave forms. Greater scatter returns are to be expected when the electric field of the impinging wave is aligned with the major axis of the tumor, such as illustrated in FIGS. 1A and 1B.

FIG. 1A illustrates a spherical, possibly benign tumor 12, with a major axis 14 and a like minor axis 16. FIG. 1B illustrates an asymmetrical tumor 18, possibly malignant, with a major axis 20 significantly greater than the minor axis 22. By rotating the electric field polarization, scattering from the minor axis of an asymmetrical tumor 18 can be reduced. By noting the ratio of the maximum scatter response to the minimum response, an assessment may be made as to the character of the observed tumor.

Further information as to the geometry of a tumor may be developed by noting the spectral distribution of the scattered waves. FIG. 2 illustrates several spectral responses in relative decibels per unit frequency as a function of frequency in Giga Hertz (GHz). For the chest wall there is a response curve 36, for a fat right circular cylinder there is a response curve 38, and for a thin right circular cylinder there is a response curve 40. All of curves 36, 38 and 40 are somewhat idealized. As illustrated, significant differences occur in the spectral response of a tumor that is similar to a right-circular cylinder of large diameter (FIG. 1A) as compared to the response from one similar to a cylinder with a small minor diameter (FIG. 1B). Spectral differences in back, side and forward scatter signals can help separate benign from malignant tumors. Also note, in FIG. 2, that the scattered response signals 36 from the patients' chest wall are an order of magnitude greater than the scatter signals from tumors 38 and 40.

These amplitude, polarization, and spectrum differences of the scattered signal returns, from an identified tumor that may be either malignant or benign, can be compared to the scattered returns of tumors with known geometry for benign tumors and for malignant tumors. The scattered returns from tumors with known geometry and characteristics can be developed on the basis of actual measurements on tumors, followed by biopsies to determine whether the tumor is benign or malignant. These data may be processed in computer format into a look-up library. Actual measured data taken during screening or diagnosis may be compared with data stored in the look-up library. The degree of correlation of the measured screening or diagnostic data from the apparent tumor in question and the data in the look-up library can be developed. The correlation information may be presented in a format that would indicate the likelihood of a tumor being benign or malignant. The reference look-up library can be augmented by data developed by other analytic means for postulated geometry associated with benign tumors and for malignant tumors.

FIG. 3 illustrates basic features of the apparatus described in the previous noted Bridges patent and pending applications. Also included in FIG. 3 are system functions needed to help determine whether or not a tumor is possibly malignant. The system 99 shown in FIG. 3 includes a microwave source 100 which, via a wave guide 101, supplies power, in the form of plural cycle high-frequency microwave pulses, to a directional coupler 102. Via a cable 103, that power is supplied to an applicator 120 which may include an array of radiating antennas. These antennas launch a focused beam into the breast 121 of a patient 122. Scattered power returns (reflected signals) are collected by antennas in the applicator 120 and supplied, via a cable 104, to the directional coupler 102. The coupler 102 helps separate the scattered power returns of applicator 120 from the applied power pulses derived from source 100, and supplies the separated scatter signals to a scatter detector 107 via a cable 106. In addition, receiving antennas other than the illuminating antennas within the applicator 120 can be used to collect responses having different polarizations from that used by the illuminating antennas in the applicator 120 or may be used to collect side and forward scatter signals. Cable 105 is used to apply such responses directly to the scatter detector 107. Scatter detector 107, via a cable 108, supplies signals to a signal processor 109. The signal processor 109 is connected, by a cable 110, to a display unit 111, which presents the locations and the tumors in three dimensional form. A scan control unit 113, via a cable 112, supplies position data signals to the display 111, and also supplies antenna control signals to the applicator 120 by means of a cable 114.

As thus far described, system 99 of FIG. 3 is essentially similar to the systems described in the aforesaid Bridges patent and applications. But further apparatus and methods are added. These include a tumor characterization control 131, which is supplied data signals from the signal processor 109 by a cable 130. Controller 131 supplies control signals to a polarization control 134 and to a sensor control 135 via cables 133 and 132, respectively. The polarization control 134 also supplies signals, via a cable 136, to select antennas in the applicator 120 that are responsive to different polarizations. The sensor selector 135 chooses the appropriate antennas to detect back, side and forward scatter, and supplies selection signals to applicator 120 via a cable 137.

The tumor characterization control 131 also supplies control signals to a bus 140. The signal processor 109 supplies data signals to a bus 141. The bus 141 supplies input data from the signal processor 109 to a sensor correlator 142 to a scatter data circuit 143, to a polarization processor 144, to a spectral processor 145, and to an amplitude/absorption processor unit 146. The bus 140 supplies signals from the tumor characterization control 131 to the sensor correlator 142 and to the processor 146. These circuits 142–146, in turn, supply data to a correlation scorer 151 via a cable bundle or bus 150. Additional data signals are supplied to the correlation score unit 151 from a look-up library 152, a data bank on past exams 153, and from an adjacent breast unit 154, using three cables 155, 156 and 157, respectively.

The amplitude/absorption processor 146 presents relevant amplitude and absorption data signals to correlation unit 151. The scatter data circuit 143, based on its input from also 141, develops an input to unit 151. The functions of the spectrum processor 145 and the polarization processor 144 are obvious; as previously noted, each has an input from bus 141. The sensor correlator 142 provides and correlates the data patterns from forward side and back scatter sensors.

The location of an abnormality, and its associated spectrum, polarization, scatter and absorption, can also be imaged for subjective interpretation by a radiologist. This can be done via the correlation score unit 151 and a cable 160 connected from unit 151 to the display 111, or directly from each of the processors to the display subsystem 111.

The functions of each of the circuits that supply input to the correlation scorer 151 are all somewhat different. The polarization processor 144 relies on data developed by the antenna system (in device 120) that are sensitive to changes in the polarization of the scatter signals as a function of the polarization of the impinging waveform. Such antenna could be a simple rectangular wave guide in the TE 01 mode that can be excited in either the vertical or horizontal modes. Other sensors could be cross-polarized dipoles, such as a Maltese Cross, which may be constructed of lossy materials to suppress reverberation. The simplest method to detect polarization anomalies is to mechanically rotate the antenna system. All-electronic options also exist; they may use combinations of electric switches, attenuators and phase shifting hybrids. For example, a combination of electronic attenuators and power dividers can be used to excite just the vertical antenna portion of a Maltese Cross antenna. Progressively increase of the excitation to the horizontal antenna while at the same time decreasing the excitation to the vertically polarized antenna can be effected. By so doing, the plane of polarization can be rotated by 90 degrees while at the same noting peaks and nulls in the scatter returns. Additionally, a combination of a power divider, a 90 degree hybrid and a cross dipole can be used to produce circular polarization, which would tend to suppress polarization sensitive responses.

The spectrum analyzer or processor 145 develops the power spectral density from the back scatter return signals from a specific voxel for a specific polarization condition. Existing computational methods are available to do this. The scatter data image processor 143 identifies abnormalities, such a large backscatter return, examines adjacent voxels for smaller returns that might be generated by vascularization, and determines any spatial trend of the vascularization toward likely blood supply sources. The amplitude-absorption processor 146 identifies any prominent abnormalities in the forward scatter or path absorption. This may be done by noting the lack of scatter returns from the chest wall or by direct sensing of the forward scatter. Regions near the anomaly are examined to identify any spatial trends of the anomaly toward likely blood supply sources.

Sensing the Scattering from Tissues Near a Tumor

The scattering characteristic of tissues near a tumor, especially those between the tumor and nearby arteries or veins, can be exploited to ascertain the nature of the tumor. Angiogenesis is associated with malignant, growing tumors. This phenomenon can change the spatial distribution of the dielectric parameters of the tissues near a malignant tumor. This change in the spatial distribution of the dielectric parameters is initiated during the early phase of the growth of a malignant tumor. Consider an incipient malignant tumor that is very small, in the order of one or two millimeters in maximum dimension. Such small tumors cannot grow unless they are supplied with oxygen and nutrients, which can only be supplied by the vascular system. An incipient malignant tumor generates a growth factor that induces blood vessels, especially capillaries, to grow toward the malignant tumor. This adds additional water content to the normal, low-water content breast tissue, and creates a spatial network of vessels that supply blood to and from the tumor. As the tumor increases in size, the network of blood vessels increases and may interconnect with tiny arteries or veins. As the tumor enlarges further, blood vessel pathways are created to allow the malignant cells to flow into the body.

Figure 4:
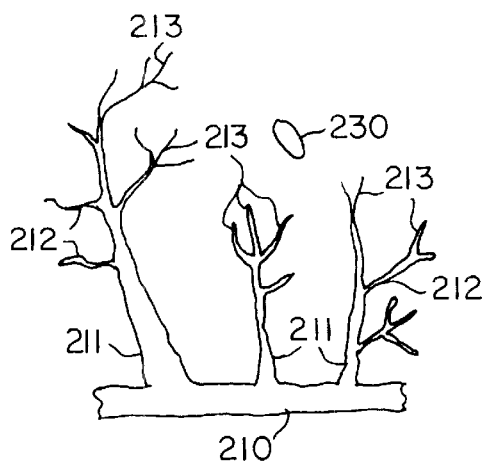
FIG. 4 is a schematic illustration of the initial stage in tumor angiogenesis.
Figure 5:
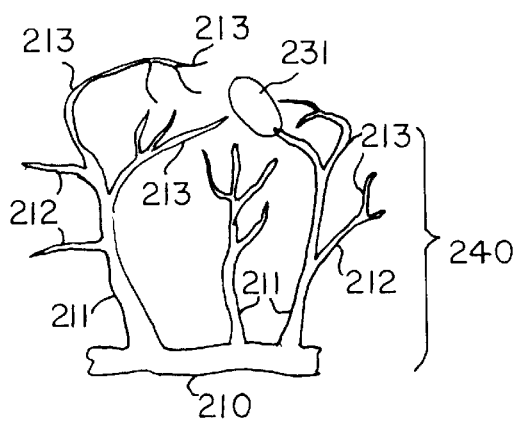
FIG. 5 is a schematic illustration, similar to FIG. 4, of a later stage of tumor angiogenesis.
Figure 6:
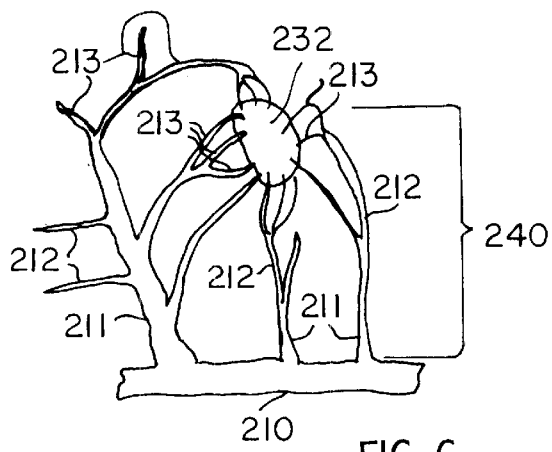
FIG. 6 is a schematic illustration, similar to FIGS. 4 and 5, of an even later stage of tumor angiogenesis.

FIG. 4 illustrates how angiogenesis begins when a malignant tumor starts. An incipient tumor 230 is shown, spaced from a large blood vessel 210. Smaller vessels 211, large capillaries 212, and tiny capillaries 213 sprout from the large blood vessel 210 into normal breast tissue. As shown in FIG. 5, the tumor 231 (now somewhat larger) has attracted a network of tiny capillaries 213 and large capillaries 212. These present a region 240 of enhanced conductivity and permitivity relative to the normal breast tissues between the malignant tumor and the large blood vessels. FIG. 6 illustrates the case where the tumor 232 metastasizes by incorporating the larger capillaries 212 and small blood vessels 211 into the body of the tumor.

The tumor may enlarge in such a way that the interior of the tumor can no longer be supplied adequately with oxygen and nutrients. This may result in necrosis of the interior of the tumor, and this creates the micro-calcifications that are detected by X-ray mammography. Such micro-calcifications are quite important for X-rays to detect tumors. The differences in the dielectric properties of the necrotic and growing malignant tissues may be used to characterize the tumor.

Benign tumors, in general, do not exhibit the angiogenesis found for malignant tumors. Because blood is highly conducting, relative to normal breast tissues, the network of blood vessels created by the malignant tumor's growth factor can be exploited not only to determine whether a tumor is malignant or not, but also to enhance the ability of the microwave system to reliably detect very small, incipient tumors.

During the early growth of a tumor, the network of capillaries surrounding the tumor will tend to create a spatial distribution of enhanced conductivity and permittivity surrounding the tumor. Such an enlargement can lead to an increase in the scattering cross section. By comparing the angiogenesis-induced microwave cross section with the cross-section of the tumor noted in earlier breast exams, the detection of a growing tumor can be determined earlier than if growth in size of the tumor is considered alone. The development of small capillaries immediately surrounding the tumor will introduce spectral, polarization, back, side and forward scatter anomalies. In addition, the microwave cross-section of the malignant tumor can be compared with the estimated size of the tumor as developed by X-ray mammography or by ultrasound. Comparing the sensed data from one breast with the adjacent breast is also possible. Such comparison can be developed with digital processing and presented in a format to aid the physician in developing the breast treatment.

Not considered in any prior patent (or in the pending Bridges applications) is sensing the nature of the network of capillaries that grow close to a malignant tumor. These may interconnect first with tiny arteries and veins and eventually to major arteries and veins. The network of capillaries will tend to be skewed to existing tiny veins or arteries, or, eventually to an artery or a vein. This will create a region of enhanced conductivity and permittivity between the tumor and available sources of blood, or drains for blood. The microwave technology previously disclosed in the Bridges patent (and in the aforesaid pending applications) can be modified and improved to detect and image the region of enhanced conductivity and permittivity. In many cases, this procedure can point to the presence of an otherwise barely detectable tumor; it will also confirm whether the tumor is likely to be malignant.

In the early stages of growth of a malignant tumor, the scattering characteristics of the expanding capillary network tend to be different than those for a spatially well defined tumor. These differences can be exploited to develop a crude image of the capillary network. First, the region will be anisotropic, wherein the scattering response will be sensitive the angle of polarization of the impinging wave.

Rather than generating substantial back scatter, the region of the expanding capillary network may have a tendency to absorb, diffuse or refract the energy of the impinging wave, rather than reflect it. Therefore, means must be considered that measures not only the scatter signals, but also their absorption, diffusion or possible refraction. The perturbation in the forward scattering of a wave that passes through the network of capillaries may be sensed for this purpose. The perturbation of the scattered waves by the network of capillaries may exhibit any number of formats. It may enhance the side or forward scatter at the expense of the back scatter or it may absorb or diffuse the penetrating wave, thereby reducing energy in the forward direction. The point is that apparatus and methods must be modified to sense the network of capillaries, regardless of the nature of the perturbation.

For illustrative purposes, consider the case where the network both absorbs and diffuses the impinging wave of microwave energy. Ignoring, for a moment, possible weak back scatter effects from the network, consider an impinging wave that progresses through the tumor and thence to the chest wall of the patient. During transit through the capillary network, some of the energy in the wave will be absorbed or diffused. Additionally, the heterogeneity of the network diffuses or redirects a portion of the energy away from the expected straight line path to the chest wall. The result is that the network will cast an ill-defined shadow onto the chest wall. What energy remains will be strongly reflected by the high water content of the muscles in the patient's chest wall back to the source of the impinging wave. This chest wall return wave will be further attenuated and diffused by a second pass through the capillary network. The presence of the capillary network may be detected by noting the absence of the back scatter returns from the chest wall.

Figure 7:
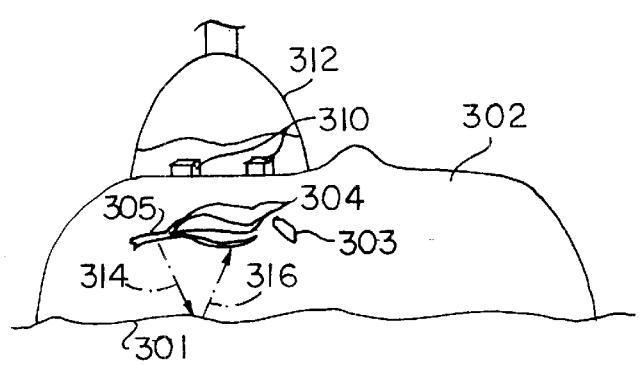
FIGS. 7 and 8 are detail illustrations, partly schematic, of two different arrangements for detection of tumor angiogenesis.

FIG. 7 illustrates the basic features just discussed. An applicator 312 that contains one or more antennas 310 is placed upon the breast 302 of a patient undergoing examination. The breast 302 contains a malignant tumor 303 that is supplied nutrients by a network of capillaries 304 that terminate in a blood vessel 305. The applicator 312 launches waves of energy that, in passing through the network of capillaries 304, is attenuated and shifted in phase. This attenuated wave, represented by arrow 314, strikes the high water content muscles in the chest wall 301 and energy is redirected back toward the applicator 312. This redirected wave, represented by arrow 316, passes through the network of capillaries and small blood vessels, and is further attenuated, thereby creating an ill-defined shadow that suggests the presence of an absorbing region.

Figure 8:
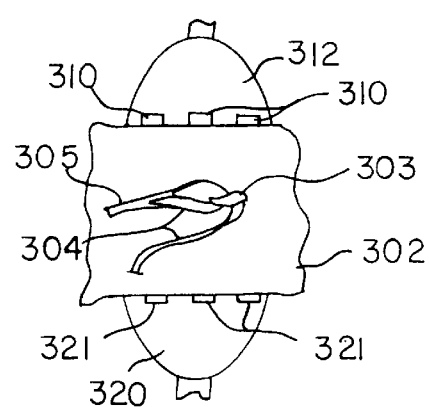

The network of capillaries and blood vessels may also be sensed by a forward scatter arrangement shown in FIG. 8. The applicator 312 and included antennas 310 is located on one side of the breast 302. Another applicator 320 and related antennas 321, operates as a collector of the energy that is launched into the breast 302 from applicator 312. The pattern of this energy is perturbed by the presence of the malignant tumor 303, the network of capillaries 304 and the blood vessel 305.

Another approach would be to detect or image discrete tiny arteries or veins. Analysis has shown that blood vessel in the order of 0.5 mm or greater in diameter can be readily imaged. The trend of such vessel would point to the location of a malignant tumor.

As another example, consider a network interconnection, in the case of a more mature malignant tumor, in the order of five mm or larger maximum dimension. This interconnection will dramatically enlarge the scattering cross-section beyond that implied by the size of the tumor and the capillary network that immediately surrounds the tumor. In this case the scattering geometry is formed by the combination of the tumor, the tiny blood vessels and the larger arteries and veins. This arrangement may dramatically enlarge the effective scattering cross-section of the tumor; it will also significantly change the polarization and spectral responses of the malignant tumor.

Figures 9, 9A:
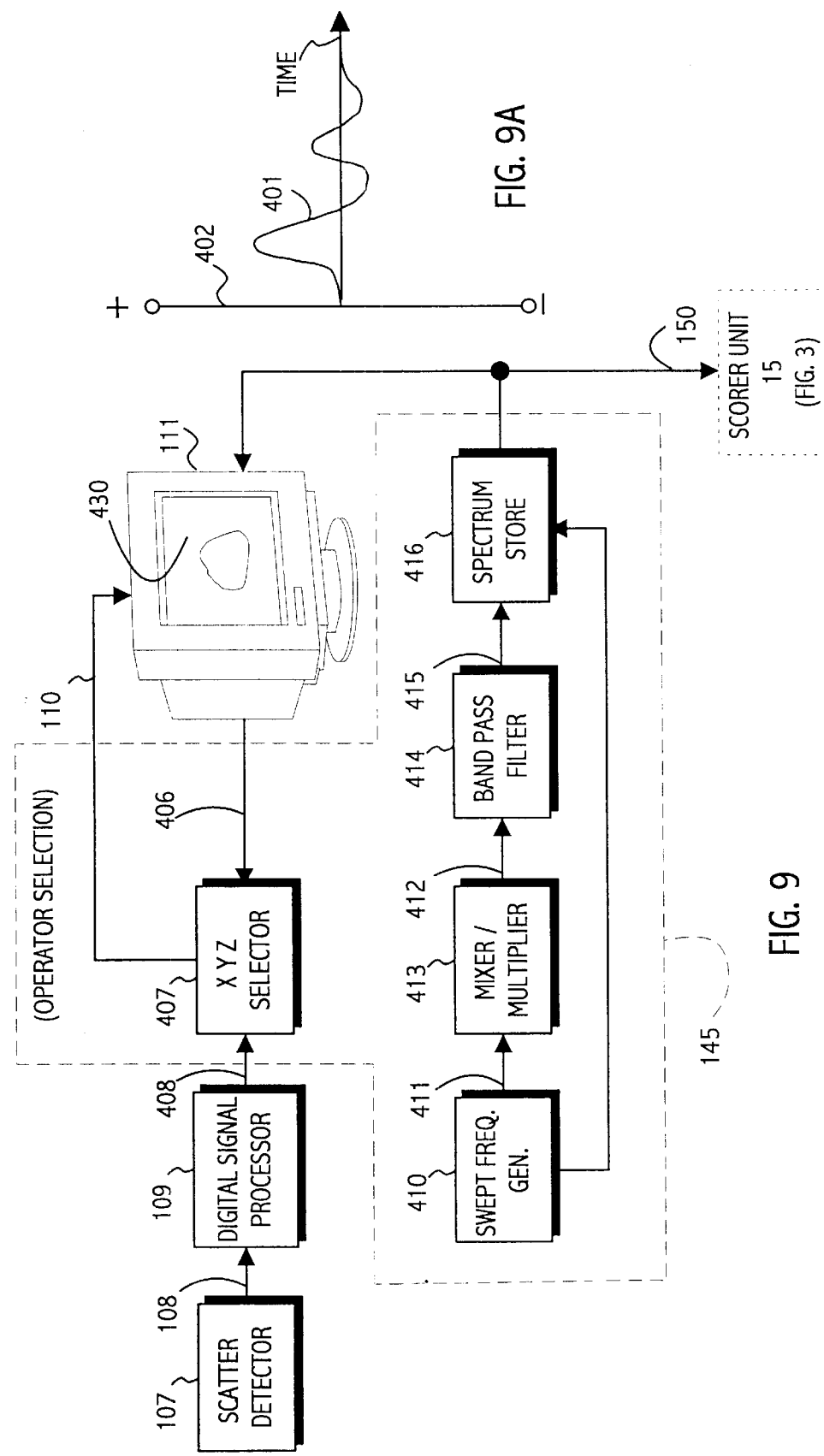
FIGS. 9 through 12 are schematic diagrams of circuit units that may be used in implementing portions of the system shown in FIG. 3.

FIGS. 9 and 9A illustrate the functional circuits and the waveform for the spectrum processor 145 of FIG. 3; some of the other circuits of FIG. 3 are included to facilitate correlation. Processor 145 develops the spectral characteristics of the returns from a specific group of voxels, such as for a tumor that is being diagnosed for malignancy. The waveform 401 of the backscatter is collected from a specific group of voxels as x, y, and z and is presented as having an amplitude 402 which is a function of time. A "fast" Fourier Transform method may be used to develop the spectral distribution of the energy as a function of the frequency. To accomplish this transform, the waveform 401 is assumed to be repeated long enough to produce the desired spectral resolution. The microwave backscatter detector 107 provides the time history of the returns from a specific antenna in the applicator 120 FIG. 3. The returns from each antenna location, via the cable 108, are then combined in the signal processor 109, to form a multi-dimensional characterization of the backscattered returns. These returns are also applied, via a cable 408, to an x, y, z processor or selector 407 that stores the selected waveform. Also, the output of the digital process 109, via the cable 110 is used to form an image of the returns in the display 111. The imaged returns from a group of one or more voxels are selected by the display operator (not shown) and, via a cable 406, applied to the digital microprocessor 407, which stores the specific backscatter returns selected by the operator for the specified voxels. Processor 407 also generates a repeated time-history sequence of the stored waveform and applies this sequences, via a cable 409, to a mixer/multiplier 412. A swept frequency generator 410 provides a swept frequency of increasing value that is applied, via a cable 411, to a multiplier or diode mixer 412. The output of mixer 412 is applied, via a cable 413, to a band pass filter 414, and thence, via a cable 415 to a microprocessor store 416 that conditions the spectrum into a format suitable for overlaying, in false color onto a portion of the displayed image of the display 111. The conditioned spectrum from circuit 416 is also supplied, via the cable 150, to the correlation scorer unit 151 (FIG. 3).

Figure 10:
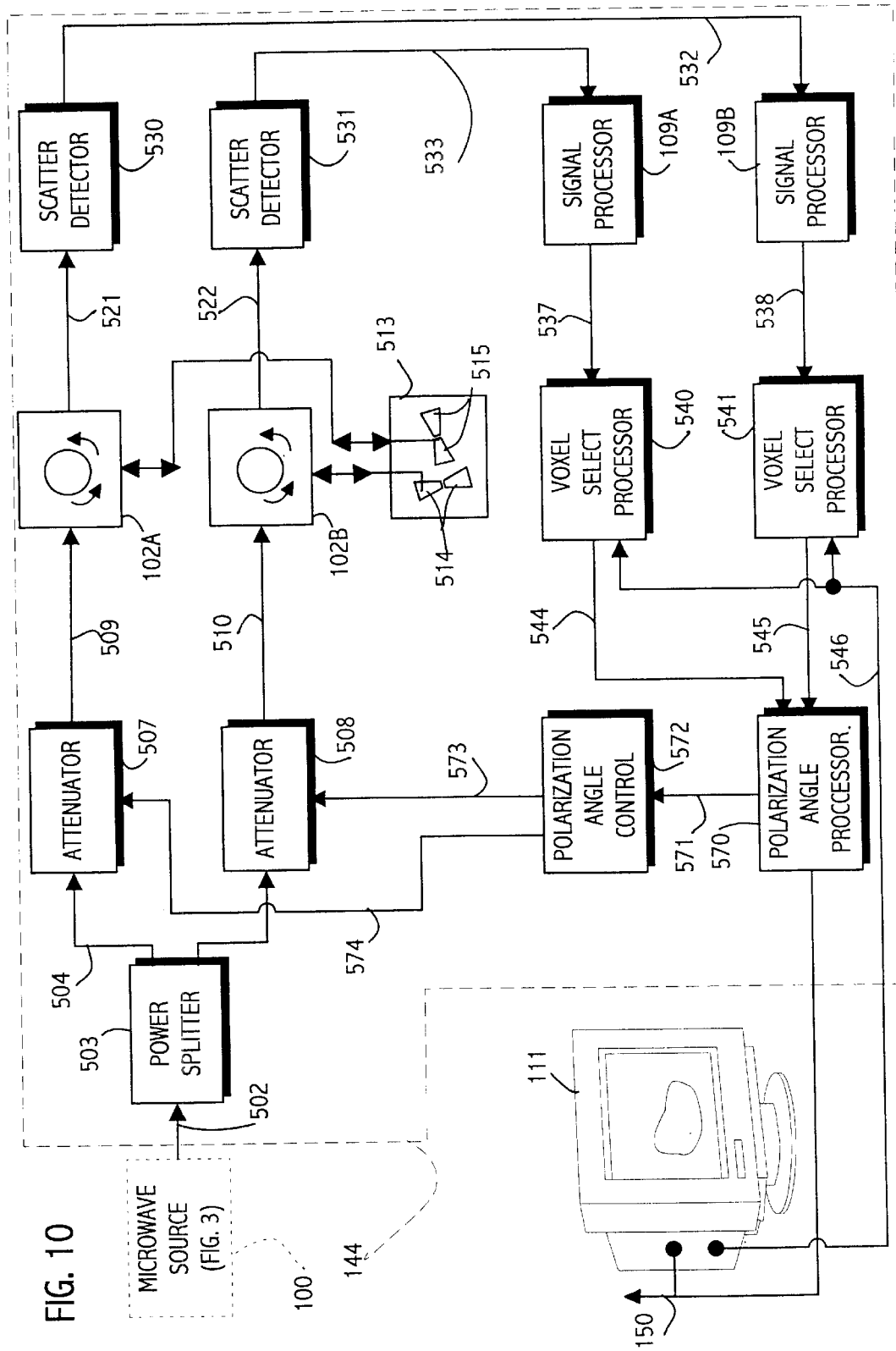

FIG. 10 illustrates the part of the system, polarization processor 145, that shows how the polarization of the scattered returns can be determined and used for diagnostic purposes. The microwave source 100 supplies power via a cable 502 to a power splitter 503, that divides the power into two equal signal values, and, via cables 504 and 505 supplies the split signal to two electronically controlled attenuators 507 and 508. The outputs of the attenuators 507 and 508 are applied to two directional couplers 102A and 102B via cables 509 and 510, respectively. One direction coupler, 102A supplies and/or accepts energy to or from a horizontal antenna 515 in an applicator 513. Directional coupler or circulator 102B supplies and collects energy to a vertical antenna 514 in the applicator. Fed via cables 521 and 522, the scattered returns for the vertical and horizontal antenna respectively are converted into a format suitable for digital processing by two scatter detectors 530 and 531 respectively. Via two cables 532 and 533, the detected scatter signals from the vertical and the horizontal antennas are applied respectively, to the signal processors 109A and 109B. Via two cables 537 and 538, the x, y, and z locations of the vertical and horizontal backscatter applied to the voxel select processors 540 and 541 respectively. An operator, not shown select the voxel region of interest on the display 111, as, by means of a mouse-controlled cursor. The image display system 111 provides selected xyz data to the voxel select processors 540 and 541. these processors in turn, via two cables 544 and 545, provide the amplitude of the scattered return from the vertical and horizontal antennas, respectively, to a polarization angle processor circuit 570. By noting the ratio the amplitudes of the vertical to horizontal return, the direction of the principal backscatter source can be developed. This may be done by varying the signal applied to the vertical or horizontal antennas such as antennas 514 and 515. For example, only the vertical antenna 514 could be excited by attenuating, via a cable 573, the power applied to the horizontal antenna and the amplitude of the vertical returns noted. Then the process could be repeated by exciting only the horizontal antennas 515, and the amplitude of the returns noted. Assuming that the amplitude of the vertical returns were very small, then the polarization of the scatter returns will be largely horizontal. If the returns are nearly equal, the angle between the amplitudes is about forty-five degrees. Other variations are possible, such as observing the results only in the frequency domain, where the phase angle of the amplitude of the returns could be included to develop additional data.

Some abnormalities under investigation may represent low-wave impedance malignant tumor; others may be regions of high, very-low water content fat. These regions or interfaces can be distinguished by developing the wave impedance of the scatterer. The phase of the amplitude of the pulse return can be used to distinguish if the scatterer has wave impedance larger or smaller than the wave impedance of the material propagating the impinging waveform. For example, if the scatterer has a higher wave impedance, suggesting lower values of dielectric parameters, the amplitude of the backscatter pulse will have the same polarity as that for the impinging pulse. If the dielectric parameters of the scatterer, such as a tumor, are larger than the propagating media, then the amplitude of the scattered return should have the opposite polarity. Further, the approximate wave impedance of the scatterer relative to the wave impedance of the media containing the impinging wave can be determined from the reflection coefficient relationship for perpendicular impingment onto planar interfaces as follows:

$$\rho=[E_r]/[E_f]=[\eta_2-\eta_1]/[\eta_2+\eta_1],$$

where $\rho$ is the reflection coefficient, $E_r$ is the electric field of the reflected wave, $E_f$ is the electric field of the forward or impinging wave, $\eta_1$ is the wave impedance of the media for the impinging wave, and $\eta_2$ is the wave impedance of the scattering media. Similar relationships can be developed for other scattering situations.

Figure 11:
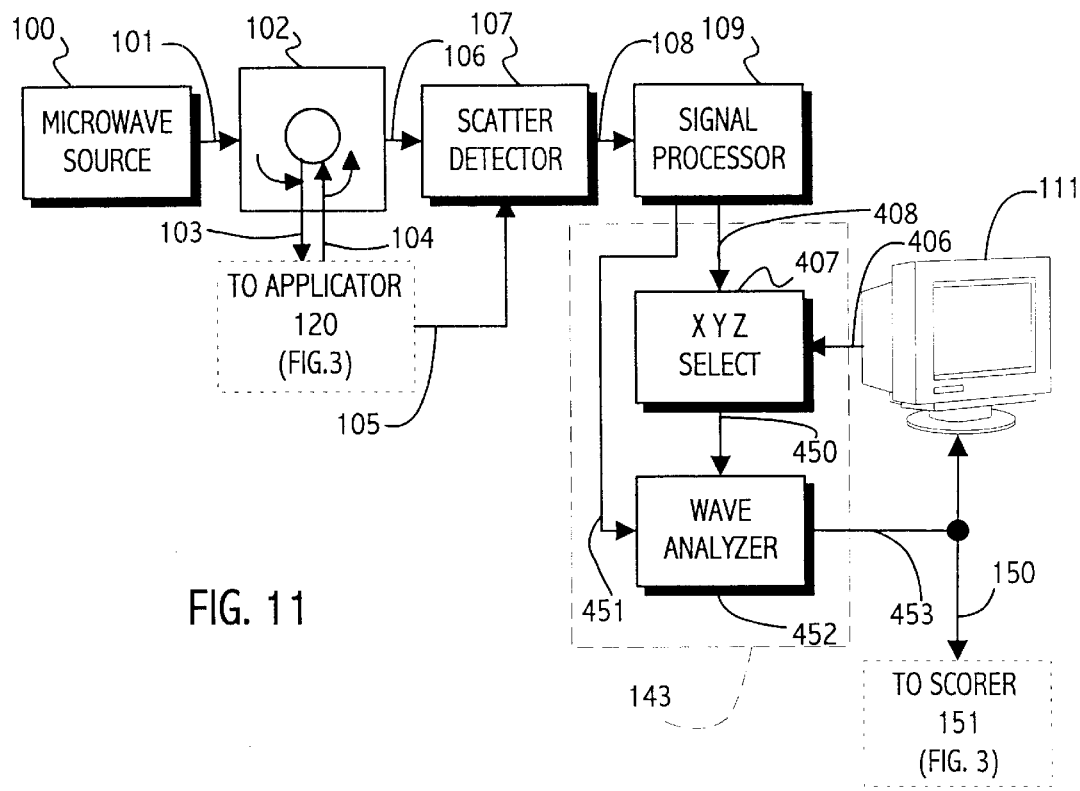

A wave impedance subsystem 143 to do this is illustrated in FIG. 11. It uses functions similar to those shown in FIGS. 3 and 9. From FIG. 3, a microwave source 100, is coupled by the cable 101 coupled to a directional coupler 102. From coupler 102 energy is supplied, via cable 103, to the applicator 120. Returns from the applicator are supplied, via cable 104, to the directional coupler 102 and thence to the scatter detector 107 via cable 106. Cable 105 also supplies backscatter energy from non-radiating antennas in the applicator 120. From FIG. 9, the system operator (not shown) selects a voxel region on the display 111. Via a cable 406, data on the voxels selected is sent and stored in the voxel-select s, y, z microprocessor 407. Via a cable 450, data on the waveforms stored in the processor 407 are presented to the wave analyzer 452. The wave analyzer 452 compares the selected waveforms with the impinging wave-forms available from the signal processor 109 via cable 451. This comparison process, similar to that described in the above equation, can be used to assess the composition of the scatterer, the incipient or suspected tumor. Such data is sent to the display 111 for overlay near the selected group of voxels, via a cable 453. Such data is also sent to the correlation scorer 151 via cable 150.

Figure 12:
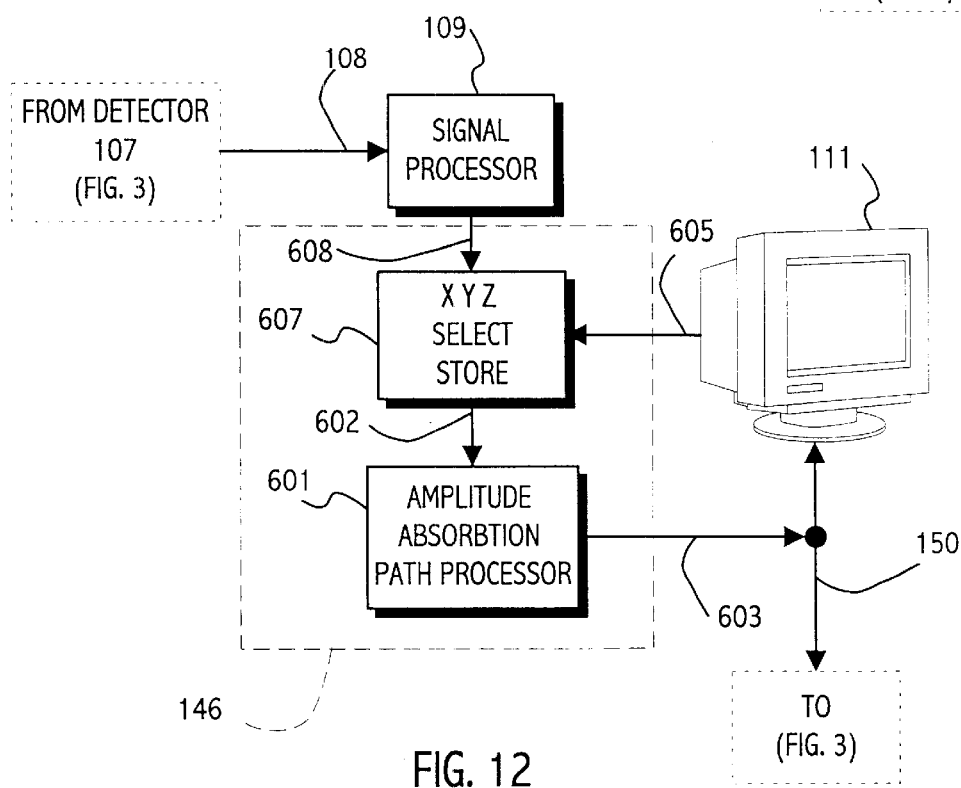

Within the breast (e.g. breast 121, FIG. 3) a region of vascularization may develop to indicate the probable presence of a malignant tumor. Such vascularization could suggest the presence of an incipient malignant tumor that is not otherwise readily detectable. However, such a network of tiny blood vessels could either scatter well or it might not scatter well, depending on the spatial distribution of the dielectric parameters. FIG. 12 shows the principal circuits for the amplitude/absorption processor subsystem 146 of FIG. 3 and illustrates how the vascular system can be processed to provide and indication of the presence of a malignant tumor. As illustrated in FIG. 3, the signal processor 109 provides data on the scatter returns in three dimensions x, y and z. As shown in FIG. 12, the signal processor 109 supplies 3-D backscatter data via a cable 608 to a voxel select (xyz) storage computer 607. The system operator, not shown, selects series of adjacent voxels from the display subsystem 111. These selected voxels may be based on the location of an abnormality being diagnosed for malignance or on an exploration of regions of questionable responses that might contain an incipient malignant tumor. The locations of blood vessels near the area in question may also be presented. Data on the selected voxels in 607 are sent to the amplitude/absorption path processor 601. Regions of prominent scatter are first developed to see if any vascular halos that might surround a malignant tumor exist. Next, likely vascular pathways that might lead to major blood vessels are developed. Such data are forwarded, via a cable 603, to the display 111. Such region might be developed on an interated basis with a series of presentations in the display and revisions based on interaction with the system operator.

The returns indicative of regions of high absorption, such as based on the returns from the chest wall, may be used in a similar manner. In this case, the backscatter from the surface of the breast could be compared with the backscatter returns from the chest wall. Any significant diminution of the backscatter returns from the chest will suggest the presence of an intervening scatterer. This scatter may generate a large backscatter and could be made readily visible on the display subsystem 111. Or it could not appear strongly on the backscatter display because the scattering region is largely absorptive and generates only minimal backscatter.

The foregoing discussions have assumed control and interaction with an experienced radiologist as system operator. However, as experience is gained in clinical trials, at least some of the interaction functions with a system operator may be assumed by additional signal processing steps.

What is claimed is:

1. A non-invasive method to detect vascularization associated with one or more malignant tumors in living tissue of a living organism, where dielectric properties of the vascularization are different than dielectric properties of normal living tissue, the method comprising:

A. generating a non-ionizing input wave within a wide band frequency range;

B. applying the input wave of step A to a field excitation antenna to illuminate a discrete volume within said living tissue of said living organism and develop scattered power returns from said discrete volume;

C. collecting at least a portion of said scattered power returns of step B by means of at least one receiving antenna;

D. detecting said scattered power returns of step C;

E. applying said detected scattered power returns of step D to a signal processor to develop a segregated signal; and F. processing said segregated signal of step E to identify the vascularization associated with one or more malignant tumors.

2. A non-invasive method to detect vascularization associated with one or more malignant tumors in living tissue of a living organism, according to claim 1, in which the following additional step is performed:

displaying characteristics of the vascularization.

3. A non-invasive method to detect vascularization associated with one or more malignant tumors in living tissue of a living organism, according to claim 2, in which:

polarization characteristics of the scattered power returns are one of the displayed characteristics.

4. A non-invasive method to detect vascularization associated with one or more malignant tumors in living tissue of a living organism, according to claim 2, in which:

spectral characteristics of the scattered power returns are one of the displayed characteristics.

5. A non-invasive method to detect vascularization associated with one or more malignant tumors in living tissue of a living organism, according to claim 2, in which:

amplitude characteristics of the scattered power returns are one of the displayed characteristics.

6. A non-invasive method to detect vascularization associated with one or more malignant tumors in living tissue of a living organism, according to claim 2, in which:

absorption characteristics of the scattered power returns are one of the displayed characteristics.

7. A non-invasive method to detect vascularization associated with one or more malignant tumors in living tissue of a living organism, according to claim 2, in which the following additional step is performed:

displaying the characteristics in a multi-dimensional format.

8. A non-invasive method to detect vascularization associated with one or more malignant tumors in living tissue of a living organism, according to claim 1, in which the following additional step is performed:

correlating said vascularization with prior data on scattered power returns associated with vascularization.

9. A non-invasive method to detect vascularization associated with one or more malignant tumors in living tissue of a living organisms according to claim 8, in which the following additional step is performed:

correlating said vascularization with prior data on polarization of scattered power returns associated with vascularization.

10. A non-invasive method to detect vascularization associated with one or more malignant tumors in living tissue of a living organism, according to claim 8, in which the following additional step is performed:

correlating said vascularization with prior data on spectral characteristics of scattered power returns associated with vascularization.

11. A non-invasive method to detect vascularization associated with one or more malignant tumors in living tissue of a living organism, according to claim 8, in which the following additional step is performed:

correlating said vascularization with prior data on amplitude characteristics of scattered power returns associated with vascularization.

12. A non-invasive method to detect vascularization associated with one or more malignant tumors in living tissue of a living organism, according to claim 8, in which the following additional step is performed:

correlating said vascularization with prior data on absorption characteristics of scattered power returns associated with vascularization.

13. A non-invasive method to detect vascularization associated with one or more malignant tumors in living tissue of a living organism, according to claim 8, in which the following additional step is performed:

developing a score that represents the likelihood of one or more malignant tumors being present.

14. A non-invasive method to detect vascularization associated with one or more milignant tumors in living tissue of a living organism, where dielectric properties of the vascularization are different than dielectric properties of normal living tissue, the method comprising:

A. generating a non-ionizing electromagnetic illumination wave within a wide band frequency range;

B. illuminating said living tissue with said illumination wave of so A in order to induce electromagnetic fields in discrete volumes that surround one or more tumors within said normal living tissue;

C. sensing pertubation of said induced electromagnetic fields caused by possible vascularization in said discrete volumes of step B;

D. collecting at least a portion of scattered power returns caused by said perturbation of step C;

E. detecting said scattered power returns of step D;

F. applying said detected scattered power return of step E to a signal processor to develop a segregated signal; and G. processing said segregated signal of step F to identify the vascularization between one or more tumors and nearby blood vessels.

15. A non-invasive method to detect vascularization associated with one or more malignant tumors in living tissue of a living organism, according to claim 14, in which the following additional step is performed:

displaying in a multi-dimensional format characteristics of said vascularization and nearby blood vessels.

16. A non-invasive method to detect vascularization associated with one or more malignant tumors in living tissue of a living organism,, according to claim 14, wherein said wide band frequency range is from 0.1 to 10 GHz.

* * * * *

UNITED STATES PATENT AND TRADEMARK OFFICE
CERTIFICATE OF CORRECTION

PATENT NO. : 6,421,550 B1
DATED : July 16, 2002
INVENTOR(S) : Jack E. Bridges, Susan Hagness, Allen Taflove and Milica Popovic It is certified that error appears in the above-identified patent and that said Letters Patent is hereby corrected as shown below:

Title page,
Item [73], Assignee, delete "Prospect" and in lieu thereof insert -- Mount Prospect --.
Item [63], Related U.S. Application Data, delete "and a division" and in lieu thereof insert -- which is a continuation-in-part --; delete "and a division" and in lieu thereof insert -- which is a continuation-in-part --.
Item [56], References Cited, delete "5,829,438" and in lieu thereof insert -- 5,829,437 --.

Drawings,
Figure 3 is corrected as follows:

Apply reference numeral 155 to the cable supply data signals from look-up library 152 to correlation scorer unit 151; apply reference numeral 156 to the cable supplying data signals from data bank on past exams 153 to correlation scorer unit 151; and apply reference numeral 157 to the cable supplying data signals from adjacent breast unit 154 to correlation scorer unit 151.

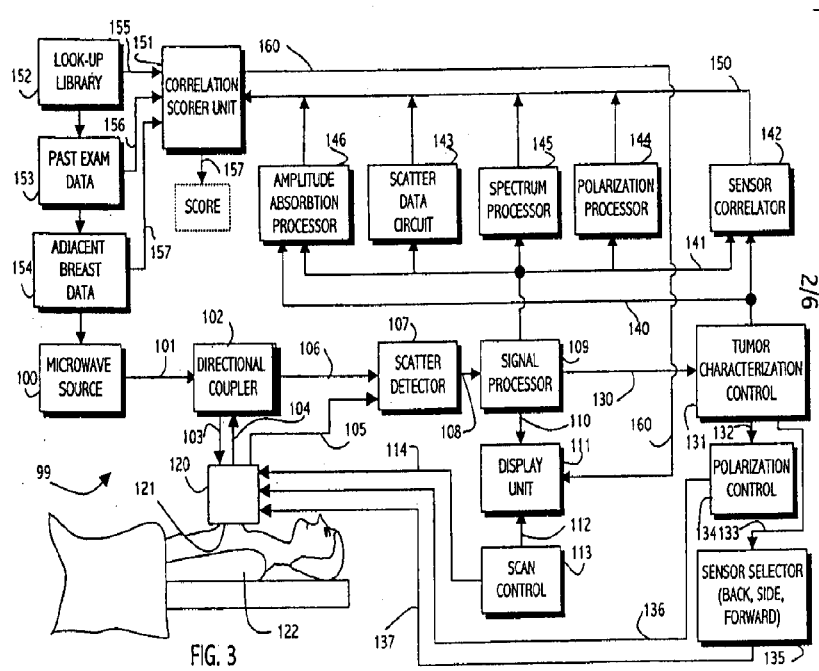

FIG. 3

UNITED STATES PATENT AND TRADEMARK OFFICE
CERTIFICATE OF CORRECTION

PATENT NO.   : 6,421,550 B1
DATED        : July 16, 2002
INVENTOR(S)  : Jack E. Bridges, Susan Hagness, Allen Taflove and Milica Popovic It is certified that error appears in the above-identified patent and that said Letters Patent is hereby corrected as shown below:

Figure 9 is corrected as follows:

Apply reference numeral 409 to the cable that applies to mixer/multiplier 412 the sequence generated by processor 407; delete reference numeral 413 from mixer/multiplier 412 and in lieu thereof apply reference numeral 412 to mixer/multiplier 412; and delete reference numeral 412 from cable 413 that applies output of mixer 412 to band pass filter 414 and in lieu thereof apply reference numeral 413 to cable 413 that applies output of mixer 412 to band pass filter 414.

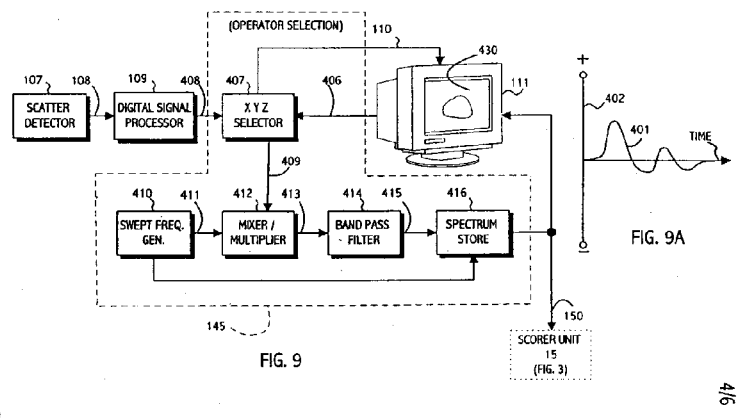

Figure 10 is corrected as follows:

Apply reference numeral 505 to the cable supplying the split signal to electronically controlled attenuator 508.

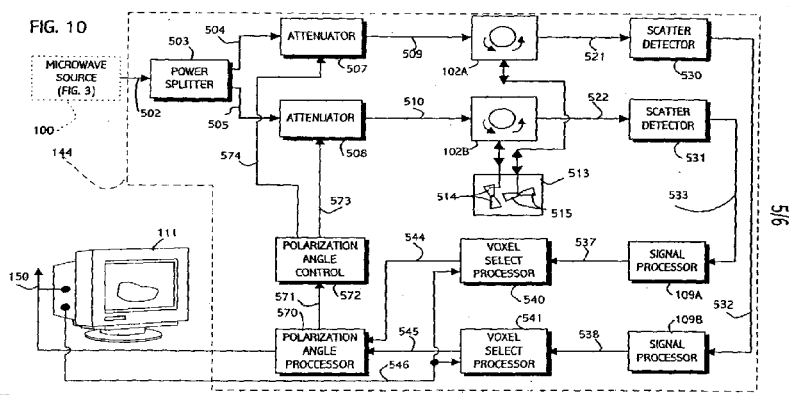

UNITED STATES PATENT AND TRADEMARK OFFICE
CERTIFICATE OF CORRECTION

PATENT NO. : 6,421,550 B1
DATED : July 16, 2002
INVENTOR(S) : Jack E. Bridges, Susan Hagness, Allen Taflove and Milica Popovic It is certified that error appears in the above-identified patent and that said Letters Patent is hereby corrected as shown below:

Column 5,
Line 19, delete "score" and in lieu thereof insert -- scorer --.

Column 9,
Line 11, delete "sequences" and in lieu thereof insert -- sequence --;
Line 46, between "data" and "to" insert -- via cable 546 --;
Line 47, delete "these" and in lieu thereof insert -- These --.

Column 12,
Line 27, delete "organisms" and in lieu thereof insert -- organism, --.
Line 60, delete "milignant" and in lieu thereof insert -- malignant --;

Column 13,
Line 2, delete "so" and in lieu thereof insert -- step --;
Line 5, delete "pertubation" and in lieu thereof insert -- perturbation --;
Line 10, delete "return" and in lieu thereof insert -- returns --.

Column 14,
Line 12, after "organism" delete ",".

Signed and Sealed this

First Day of April, 2003

JAMES E. ROGAN
*Director of the United States Patent and Trademark Office*